US012396689B2

(12) United States Patent
Shen et al.

(10) Patent No.: US 12,396,689 B2
(45) Date of Patent: Aug. 26, 2025

(54) DETERMINING NEEDLE POSITION

(71) Applicant: KONINKLIJKE PHILIPS N.V., Eindhoven (NL)

(72) Inventors: Yanhua Shen, Shenyang (CN); Ling Fu, Shenyang (CN); Yue Ma, Shenyang (CN); Di Zhang, Shenyang (CN); Lan Zhang, Shenyang (CN); Yue Zheng, Shenyang (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 395 days.

(21) Appl. No.: 18/010,881

(22) PCT Filed: Jun. 21, 2021

(86) PCT No.: PCT/EP2021/066775
§ 371 (c)(1),
(2) Date: Dec. 16, 2022

(87) PCT Pub. No.: WO2022/002656
PCT Pub. Date: Jan. 6, 2022

(65) Prior Publication Data
US 2023/0225684 A1    Jul. 20, 2023

(30) Foreign Application Priority Data

Jun. 28, 2020   (WO) ................ PCT/CN2020/098386
Sep. 25, 2020   (EP) ................... 20198346.7

(51) Int. Cl.
*A61B 6/12*    (2006.01)
*A61B 6/46*    (2024.01)
*G06T 7/73*    (2017.01)

(52) U.S. Cl.
CPC ................ *A61B 6/12* (2013.01); *A61B 6/463* (2013.01); *G06T 7/74* (2017.01);
(Continued)

(58) Field of Classification Search
CPC .. A61B 6/12; A61B 6/463; G06T 7/74; G06T 2207/10081; G06T 2207/20036; G06T 2207/20221; G06T 2207/30241
See application file for complete search history.

(56) References Cited

U.S. PATENT DOCUMENTS 6,487,431 B1    11/2002   Iwano
7,245,958 B1 *   7/2007   Navab ................ A61B 17/3403
                                                          600/407
(Continued)

FOREIGN PATENT DOCUMENTS

JP    2000083941 A    3/2000
JP    2013154161 A    8/2013

OTHER PUBLICATIONS

PCT International Search Report, International application No. PCT/EP2021/66775, Aug. 27, 2021.

*Primary Examiner* — Shefali D Goradia
(74) *Attorney, Agent, or Firm* — Larry Liberchuk

(57) ABSTRACT

In an embodiment, a method (100) is described. The method comprises receiving (102) data corresponding to a plurality of radiographic imaging slices of a body. The method further comprises determining (104) a position of a needle inserted in the body. The determination is based on combining information from at least one of the radiographic imaging slices comprising an indication of a first portion of the needle outside the body and at least one other of the radiographic imaging slices comprising an indication of a second portion of the needle inside the body. A combined needle region is generated by merging data corresponding to a position of the first portion of the needle outside the body with data corresponding to a position of the second portion of the needle inside the body. The method further comprises generating (106) display data for providing a visual representation of the needle in an image of the body in combi- (Continued)

nation with a visual representation of at least the first and second portions of the needle superimposed on the image. The image is in a plane that is digitally tilted with respect to a plane parallel to the plurality of radiographic imaging slices.

14 Claims, 9 Drawing Sheets

(52) U.S. Cl.
CPC .............. *G06T 2207/10081* (2013.01); *G06T 2207/20036* (2013.01); *G06T 2207/20221* (2013.01); *G06T 2207/30241* (2013.01)

(56) References Cited

U.S. PATENT DOCUMENTS

| | | |
|---|---|---|
| 11,302,435 B2 * | 4/2022 | Long .................... G16H 30/40 |
| 2007/0100234 A1 | 5/2007 | Arenson |
| 2008/0269778 A1 | 10/2008 | Patti |
| 2012/0281903 A1 | 11/2012 | Trumer |
| 2012/0302873 A1 * | 11/2012 | Tajima .................. A61B 6/502 |
| | | 600/424 |
| 2014/0086470 A1 | 3/2014 | Mukumoto |
| 2014/0270441 A1 | 9/2014 | Baker |
| 2017/0000567 A1 | 1/2017 | Kim |
| 2020/0054295 A1 | 2/2020 | Joskowicz |

\* cited by examiner

DETERMINING NEEDLE POSITION

TECHNICAL FIELD OF THE INVENTION

The invention relates to methods, apparatus and a tangible machine-readable medium for determining a needle position, for example, during a computed tomography (CT) guided interventional procedure.

BACKGROUND OF THE INVENTION

A subject's body may be imaged, for example, using a CT imaging apparatus as part of an interventional procedure such as CT-guided puncture biopsy where a needle is inserted in the body during imaging. A user such as a doctor or radiographer may need to identify a position of the needle in the subject's body. Radiographic imaging slices obtained by the CT imaging apparatus may provide an indication of the position of the needle in the subject's body. For example, the radiographic imaging slices may provide information regarding the direction of the needle, position of the needle tip and/or the needle entry point on the subject's skin surface. This information may help to provide guidance for the user to determine a needle angle (or needle trajectory) offset from a planned needle path, the distance of the needle tip from a target such as a lesion in the body and/or the length of needle that has already been inserted.

CT-guided puncture biopsy of lesions makes use of CT radiographic imaging slices, which provide detailed information for the user to make certain decisions regarding the biopsy. For example, CT radiographic imaging slices may provide high density resolution and spatial resolution, enable accurate location of lesions, and facilitate a clear understanding regarding the situation of soft tissues inside and around lesions, for example, so as to avoid certain structures or necrotic tissues.

In certain interventional procedures, the user may obtain two-dimensional radiographic imaging slices taken along an axial imaging plane in order to observe biopsy targets on a user interface. The user may rely on their experience to plan the interventional path based on an analysis of multiple radiographic imaging slices taken along the axial plane and/or the user may perform an interventional procedure with physical tilt where the imaging apparatus is tilted with respect to the subject's body to obtain a radiographic imaging slice along a specified plane, which may be different to the axial plane.

Planning and executing the interventional procedure may be a relatively time-consuming task since complete information regarding the position of the needle may not be identifiable from a single radiographic imaging slice. For example, one radiographic imaging slice may contain information regarding the tip of the needle whereas another radiographic imaging slice may contain information regarding another part of the needle. Thus, the actual interventional path may cross multiple radiographic imaging slices. Therefore, it may not be possible to display the complete interventional path on the user interface in a single image. The user may therefore rely on their experience and/or obtain additional radiographic imaging slices to ensure that the user can accurately identify the needle position. However, additional scanning takes time and may increase the radiation dose.

A user viewing one radiographic imaging slice at a time may find it challenging and/or time consuming to establish the information needed to safely and/or reliably execute the interventional procedure since multiple radiographic imaging slices may need to be assessed before deciding how to proceed with the interventional procedure.

SUMMARY OF THE INVENTION

Aspects or embodiments described herein relate to improving the determining and/or visualization of a needle position in a body. Aspects or embodiments described herein may obviate one or more problems associated with planning and executing an interventional procedure using radiographic imaging slices.

In a first aspect, a method is described. The method is a computer-implemented method. The method comprises receiving data corresponding to a plurality of radiographic imaging slices of a body. The method further comprises determining a position of a needle inserted in the body. The determination may be based on combining information from at least one of the radiographic imaging slices comprising an indication of a first portion of the needle outside the body and at least one other of the radiographic imaging slices comprising an indication of a second portion of the needle inside the body. Determining the position of the needle comprises generating a combined needle region by merging data corresponding to a position of the first portion of the needle outside the body with data corresponding to a position of the second portion of the needle inside the body. The method further comprises generating display data for providing a visual representation of the needle in an image of the body in combination with a visual representation of at least the first and second portions of the needle superimposed on the image. The image is in a plane that is digitally tilted with respect to a plane parallel to the plurality of radiographic imaging slices.

In some embodiments, the method comprises causing a user interface to display the image.

In some embodiments, determining the position of the needle comprises fitting a line to a plurality of regions in the received data indicative of the position of the first and second portions of the needle.

In some embodiments, determining the position of the needle comprises determining a real needle region from a plurality of candidate needle regions. The real needle region may be determined by minimizing an energy function derived from the received data.

In some embodiments, the energy function is based on at least one of: a discrete degree of the candidate needle region; an area of the candidate needle region; an average pixel value of an edge of the candidate needle region; an average pixel value of an inner part of the candidate needle region; a mean of all cross-sectional values of the candidate needle region; a circularity parameter; and a deviation parameter.

In some embodiments, the method comprises identifying the first portion of the needle outside the body by performing morphological opening on the received data corresponding to the first portion of the needle. The method may further comprise determining a three-dimensional region corresponding to the first portion of the needle based on a planned path for the needle. The three-dimensional region may comprise a plurality of candidate needle regions from which the real needle region can be determined.

In some embodiments, the method comprises identifying the second portion of the needle inside the body by performing threshold truncation on the received data corresponding to the second portion of the needle. The method may comprise determining a three-dimensional region corresponding to the second portion of the needle based on a planned path for the needle. The three-dimensional region may comprise a plurality of candidate needle regions from which the real needle region can be determined.

In some embodiments, the method comprises extending the three-dimensional region corresponding to the second portion of the needle. Extending the three-dimensional region may comprise searching for at least one neighboring candidate needle region removed by the threshold truncation. Extending the three-dimensional region may comprise including data corresponding to a neighboring candidate needle region as part of the extended three-dimensional region.

In some embodiments, the method comprises detecting a tip of the needle. Detecting the tip may be based on a comparison of a measurement within a candidate needle tip region within the data with a threshold indicative of a lack of presence of needle structure within the candidate needle tip region.

In some embodiments, if the comparison with the threshold is indicative of needle structure being present in the candidate needle tip region, another candidate needle tip region may be identified from the data to determine whether or not the other candidate needle tip region comprises data indicative of the presence of needle structure. If the comparison with the threshold is indicative of lack of presence of needle structure within the data corresponding to the candidate needle tip region, a previously-identified candidate needle tip region comprising data indicative of the presence of needle structure within the previously-identified candidate needle tip region may be determined to contain the tip of the needle.

In some embodiments, the method comprises detecting an insertion point on the body for the needle. Detecting the insertion point may be based on a first line fitted to a predicted trajectory of the needle. The predicted trajectory of the needle may be determined based on the determined position of the needle and a second line fitted along a surface of the body.

In some embodiments, the method comprises causing a user interface to provide an indication of a difference between a predicted trajectory and a planned trajectory of the needle. The indication of the difference may be provided responsive to a determination that there is a deviation between the predicted trajectory and the planned trajectory.

In a second aspect, a method is described. The method is a computer-implemented method. The method comprises receiving data corresponding to at least one radiographic imaging slice of a body comprising information indicative of a position of a needle inserted in the body. The method further comprises determining a predicted trajectory of the needle based on the information. The method further comprises generating display data for providing a visual representation of the needle in an image plane parallel to a line comprising the predicted trajectory of the needle, wherein the image plane is tilted with respect to the at least one radiographic imaging slice of the body.

In a third aspect, apparatus is described. The apparatus is for visualizing a needle inserted in a body. The apparatus comprises a processing unit configured to implement the method of any aspect or embodiment of the first and/or second aspect. The apparatus may determine a position of the needle. The apparatus further comprises a display unit configured to display an image of the body superimposed with the position of the needle.

In a fourth aspect, a tangible machine-readable medium is described. The tangible machine-readable medium comprises instructions which, when executed on at least one processor, cause the at least one processor to implement the method of any aspect or embodiment of the first and/or second aspect.

These and other aspects of the invention will be apparent from and elucidated with reference to the embodiment(s) described hereinafter.

BRIEF DESCRIPTION OF DRAWINGS

Exemplary embodiments of the invention will now be described, by way of example only, with reference to the following drawings, in which.

DETAILED DESCRIPTION OF THE EMBODIMENTS

Figure 1:
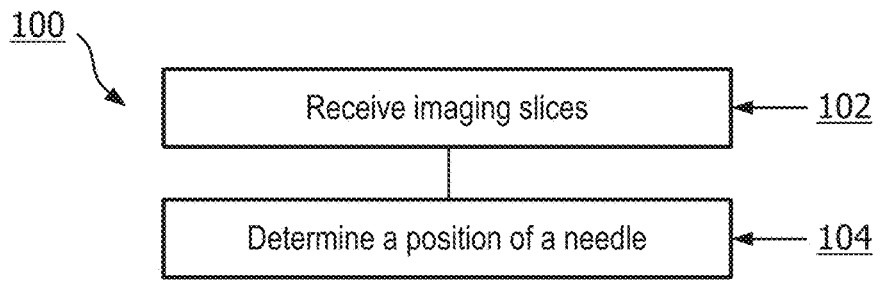
FIG. 1 refers to a method of determining a position of a needle according to an embodiment.

FIG. 1 shows a method 100 (e.g., a computer-implemented method) of determining a needle position in a body of a subject. The method 100 may be implemented by a computer such as a user computer communicatively coupled to a user interface, or a server or cloud-based service (e.g., communicatively coupled to the user computer and/or user interface).

The method 100 comprises receiving, at block 102, data corresponding to a plurality of radiographic imaging slices of a body. The plurality of radiographic imaging slices may be obtained by causing a CT imaging apparatus to image multiple parallel cross-sections of the body. The CT imaging apparatus may be communicatively coupled to the computer implementing the method 100 in order to cause the CT imaging apparatus to perform imaging and/or to receive the data from the CT imaging apparatus. The computer implementing the method 100 may be separate to, or the same as, the computer used to construct the radiographic imaging slices for visualization by a user interface.

The plurality of radiographic imaging slices may be parallel to each other. The radiographic imaging slices may be obtained for a certain plane with respect to the body. For example, the radiographic imaging slices may be taken in an axial plane which is perpendicular to the long axis defined by the length of the body. The data obtained in relation to the radiographic imaging slices corresponding to the axial plane (or another plane) may be transformed, via multiplanar reconstruction (MPR), to enable visualization of the body in different planes such as the sagittal plane, the coronal plane or another plane. In any case, when generating data for reconstructing a visual representation of the body imaged by the imaging apparatus, the data from the plurality of radiographic imaging slices may be combined or merged to create a three-dimensional representation of the imaged part of the body which can be displayed on a user interface.

The method 100 further comprises, at block 104, determining a position of a needle inserted in the body based on combining information from at least one of the radiographic imaging slices comprising an indication of a first portion of the needle outside the body and at least one other of the radiographic imaging slices comprising an indication of a second portion of the needle inside the body. Determining the position of the needle comprises generating a combined needle region by merging data corresponding to a position of the first portion of the needle outside the body with data corresponding to a position of the second portion of the needle inside the body.

The method 100 further comprises, at block 106, generating display data for providing a visual representation of the needle in an image of the body in combination with a visual representation of at least the first and second portions of the needle superimposed on the image. The image is in a plane that is digitally tilted with respect to a plane parallel to the plurality of radiographic imaging slices.

When performing an interventional procedure, a needle may be inserted into the body at a trajectory (i.e., direction) that is specified by the user. This trajectory may be determined according to the experience of the user according to the clinical scenario, for example, to avoid certain tissue in the body. In the case that the radiographic imaging slices are taken in the axial plane and the needle trajectory is tilted with respect to the axial plane, different parts of the needle may be detected in each of the radiographic imaging slices. In other words, a single radiographic slice may not contain all of the information regarding the position of the needle.

By combining the information from the radiographic imaging slices regarding the first portion of the needle outside the body with the information regarding the second portion of the needle inside the body, the position of the needle can be determined. The position of the needle may provide information regarding the length of the needle inserted in the body, the distance of the needle tip (or 'point') from a target such as a lesion in the body, the trajectory (or direction) of the needle with respect to certain features (such as certain tissue) of the body, an entry point for the needle on the surface of the body.

Since the information refers to both the first portion and the second portion, from which the trajectory of the needle can be determined (e.g., based on the relative difference in position of the first and second portion), it is possible to determine the position of the needle more easily or accurately than if viewing a single radiographic imaging slice at a time (e.g., on a user interface).

According to the method 100, a digital tilt procedure may be used to generate an image. The digital tilt procedure is described in more detail below in relation to FIG. 9.

Figure 2:
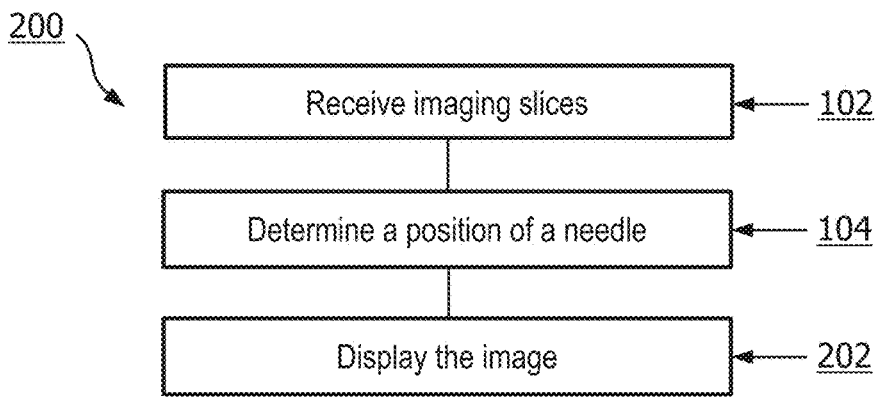
FIG. 2 refers to a method of determining a position of a needle according to an embodiment.

FIG. 2 shows a method 200 (e.g., a computer-implemented method) of determining a needle position in a body of a subject (which may be used to facilitate visualization of the needle in an image). The method 200 may be implemented by a computer such as a user computer communicatively coupled to a user interface, or a server or cloud-based service (e.g., communicatively coupled to the user computer and/or user interface). In some embodiments, the method 200 may be combined with the method 100 of FIG. 1. Accordingly, the blocks 102 to 106 of FIG. 1 are shown in FIG. 2 for ease of reference.

In some embodiments, the method 200 comprises causing, at block 202, a user interface to display the image (e.g., from the display data generated at block 106 of the method 100) of the body in combination with a visual representation of at least the first and second portions of the needle (e.g., a sufficient length of the needle may be displayed such as the entire needle length to enable the user to determine the trajectory of the needle) superimposed on the image. In some embodiments, the image displayed on the user interface may comprise an MPR image and/or a three-dimensional reconstruction of the body which can be arbitrarily rotated according to user need. When viewing the image, the user may be able to make a decision as to how to proceed with the interventional procedure. Since more information about the situation of the needle may be apparent from the image, the user may be able to implement the interventional procedure more accurately, quickly and/or efficiently than if viewing an image which contains partial information regarding the needle such as may be the case when viewing individual radiographic imaging slices. The user interface may be automatically updated as the interventional procedure continues responsive to further data being received from the imaging apparatus.

In some embodiments, determining the position of the needle comprises merging data corresponding to a position of the first portion of the needle outside the body with data corresponding to a position of the second portion of the needle inside the body. The merged data may be used to generate a combined needle region from the received data. The method 100 may further comprise using the combined needle region to determine the position of the needle.

In some embodiments, determining the position of the needle comprises fitting a line to a plurality of regions in the received data indicative of the position of the first and second portions of the needle. If the (relative) position of the first and second portions can be established, it may be possible to determine the trajectory of the needle. By fitting a line to the part of the data indicative of the position of the first and second portions, the trajectory of the needle may be determined.

Figure 3:
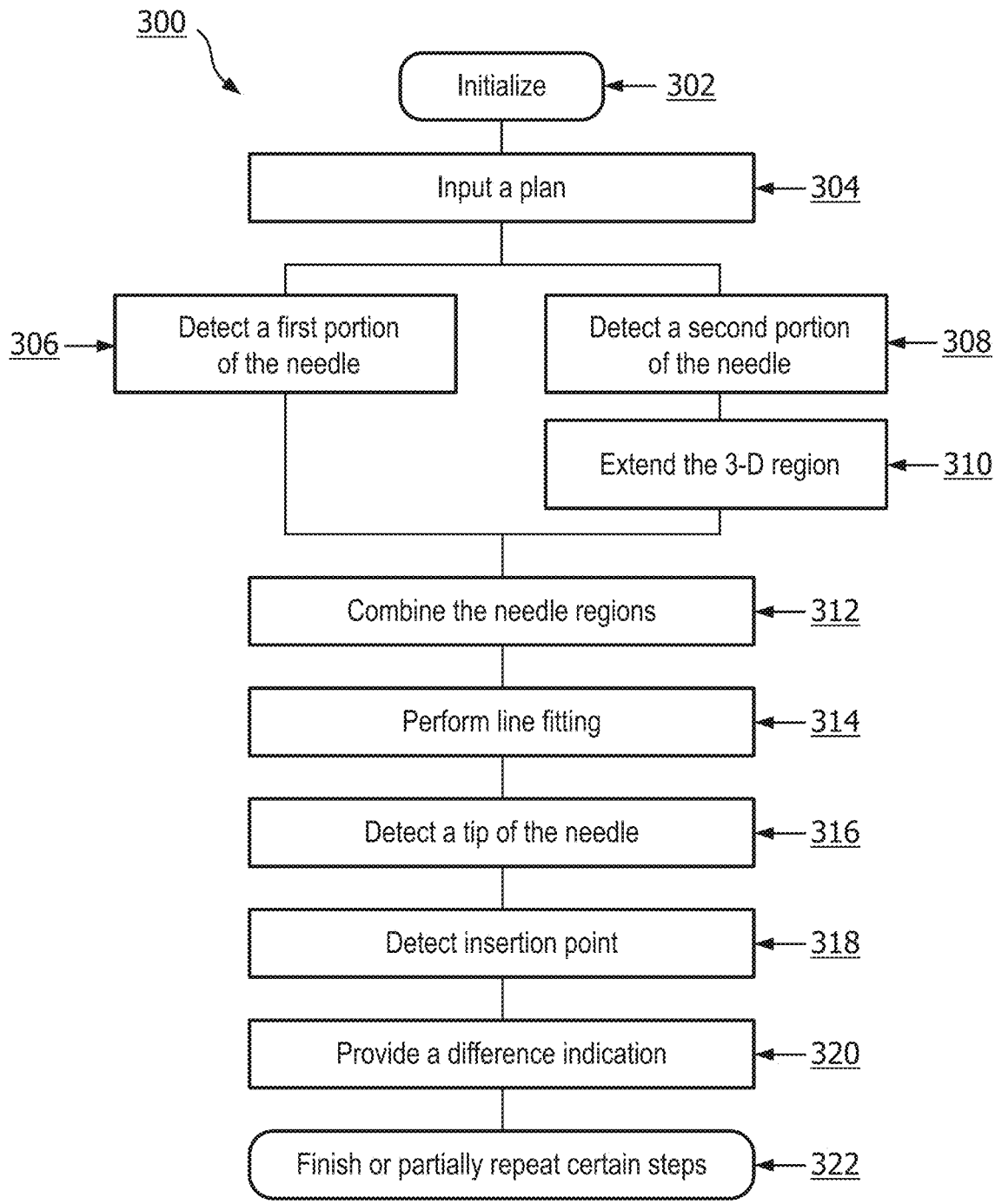
FIG. 3 refers to a method of determining a position of a needle according to an embodiment.

FIG. 3 shows a method 300 (e.g., a computer-implemented method) of determining a needle position in a body of a subject. The method 300 may be implemented by a computer such as a user computer communicatively coupled to a user interface, or a server or cloud-based service (e.g., communicatively coupled to the user computer and/or user interface). In some embodiments, the method 300 comprises the method 100 and/or method 200.

The method 300 is initialized at block 302. Further blocks of the method 300 are described below.

At block 304 of the method 300, the user may input a plan for the interventional procedure. For example, previous imaging by the imaging apparatus and/or a physical examination of the body may provide the user with information to enable them to make a plan as to how to carry out the interventional procedure. This plan may comprise a target point (e.g., a lesion in the body) and an entry point on the surface of the body. Providing the entry point is accurately targeted, certain methods described herein may provide sufficient information for the user to be able to determine the trajectory of the needle upon insertion to the body so that the user may determine if a change to the trajectory is needed to reach the target point according to the plan. Further, certain methods described herein may provide information regarding the length of the needle inserted into the body and/or the position of the needle tip so that the user may be able to determine how far away the needle tip is from the target point.

At block 306 of the method 300, the first portion of the needle is detected. At block 308 of the method, the second portion of the needle is detected. Blocks 306 and 308 may be performed in any order and may be implemented based on the data received from the imaging apparatus (e.g., at block 102 of the method 100).

In some embodiments, block 306 of the method 300 comprises identifying the first portion of the needle outside the body by performing morphological opening (or any other appropriate image processing algorithm may be performed) on the received data corresponding to the first portion of the needle (e.g., to extract the needle region outside the body and any other region that appears to look like a needle). The method 300 further comprises determining a three-dimensional region corresponding to the first portion of the needle based on a planned path for the needle. The three-dimensional region may comprise a plurality of candidate needle regions from which the real needle region can be determined. For example, a region of interest may be based on a planned path and this region of interest may be extended to a volume of interest comprising the plurality of candidate needle regions (each candidate needle region may be labeled 'i' in the description below).

A candidate needle region may comprise a region (e.g., area) of pixels in the data (from each radiographic imaging slice). The candidate needle region may or may not have a fixed size or shape. However, certain conditions on the size or shape may depend on the configuration of the CT imaging apparatus. Among a plurality of candidate regions, a region most like a needle may be determined as a 'real needle region' via an energy calculation, as described below.

In some embodiments, candidate needle regions may be filtered based on the pixel value in the data since outside the body there may be large difference in pixel value between data points corresponding to the needle (which may be metallic) and other data points corresponding to other components. For example, filtering may comprise comparing the detected pixel values with a threshold pixel value and ignoring any candidate needle regions which do not appear to correspond to the presence of needle structure.

In some embodiments, block 308 of the method 300 comprises identifying the second portion of the needle inside the body by performing threshold truncation (or any other appropriate image processing algorithm may be performed) on the received data corresponding to the second portion of the needle. The method 300 further comprises determining a three-dimensional region corresponding to the second portion of the needle based on a planned path for the needle. As referred to in block 306, the three-dimensional region may comprise a plurality of candidate needle regions from which the real needle region can be determined.

In some embodiments, method 300 comprises, at block 310, extending the three-dimensional region corresponding to the second portion of the needle by searching for at least one neighboring candidate needle region removed by the threshold truncation and including data corresponding to a neighboring candidate needle region as part of the extended three-dimensional region.

In some embodiments, determining the position of the needle comprises determining a real needle region from a plurality of candidate needle regions by minimizing an energy function derived from the received data.

In some embodiments, the energy function is based on at least one of: a discrete degree of the candidate needle region; an area of the candidate needle region; an average pixel value of an edge of the candidate needle region; an average pixel value of an inner part of the candidate needle region; a mean of all cross-sectional values of the candidate needle region; a circularity parameter; and a deviation parameter.

In some embodiments, the circularity parameter may be based on whether or not the candidate needle region is circular. In other similar words, the circularity parameter may provide an indication as to whether or not the candidate needle region is circular by its magnitude.

In some embodiments, the deviation parameter may be based on whether or not there is a deviation between a planned trajectory for the needle and a measured trajectory for the needle.

A description of the calculation of the energy function and how this is used to determine the needle region is now given. The calculation may be performed in the two blocks 306, 308 described above.

In the case of block 306 (for the part of the needle outside the body), in some embodiments, the energy function may be expressed as:

$$E(i) = e(i) + \alpha * (a(i) - \overline{a}) + \beta * (d(i) - \overline{d}) + \gamma * (n(i) - \overline{n}) + \delta * (c(i) - \overline{c}) + \varepsilon * r(i) + \theta * v(i), \text{ where}$$

$$c(i) = \frac{1}{N_i} \sum_{j=1}^{N_i} \frac{4 * \pi * \text{Area}_j}{P_j^2}, \text{ and}$$

$$r(i) = \frac{S_i}{L_i},$$

and where $\alpha$, $\beta$, $\gamma$, $\delta$, $\varepsilon$, $\theta$ are the weight for each feature. The weight for each feature may be a fixed value determined from experiments. $e(i)$ is the discrete degree of candidate needle region i. The discrete degree may refer to how the points of a region are distributed or gathered into a line. If the points distribute evenly in space, then the value $e(i)$ is low whereas if the points form a line, then the value $e(i)$ is high. $a(i)$, $d(i)$, $c(i)$, and $n(i)$ refer to the average of all the data points calculated on cross-section ($j \in \{1, 2, \ldots N_i\}$) perpendicular to i's direction. Here, i refers to a three-dimensional candidate needle region which comprises multiple cross-sections and j refers to a cross-section of this region. $a(i)$ is the average circular area (i.e., of the candidate needle region) and $d(i)$ is the average pixel value of edge (i.e., of the candidate needle region). $n(i)$ is the average pixel value of inner region (i.e., of pixels not at the edge of the candidate needle region). $r(i)$ describes whether the area is circular or not (i.e., a 'circularity parameter'). For a region 'i', $c(i)$ is the mean of all cross-sections js' values. For example, see the equations above, where $P_j$ is the perimeter of a certain candidate needle region i's cross-sectional region j, $S_i$ and $L_i$ are short axis and long axis respectively of the region projected along the regional direction, which refers to the needle direction for the real needle region (for other candidate needle regions, the regional direction refers to the region's longest direction). v(i) is the deviation of plan direction and real direction (i.e., a 'deviation parameter'). $\bar{a}$, $\bar{d},\bar{n},\bar{c}$ are the standard value for each feature. These 'standard values' refer to fixed values (e.g., from experience). For example, the standard value may refer to the value that the real needle region is considered most likely to possess. By subtracting the 'standard values' from the calculation values, the real needle region would have the smallest value for E(i).

Once the energy function has been determined, the optimization problem is performed to obtain the real needle region from the plurality of candidate needle regions, i.e., $$\arg \min E(i).$$

The procedure for obtaining the real needle region for the part of the needle inside the body is similar to obtaining the real needle region for the part of the needle outside the body. However, threshold truncation is instead of morphological opening when extracting the candidate needle regions and the energy function is different due to differences between the data for the needle inside the body and outside the body. In some embodiments, the energy function is expressed as:

$$E(i)=e(i)+\delta^*(c(i)-\bar{c})+\varepsilon^*r(i)+\theta^*v(i),$$

where the terms in the expression are described above. In block 310, neighborhood searching may be used to extend needle region in view of the previous threshold truncation processing (which may otherwise cause omission of certain regions of interest). Again, the optimization problem is performed to obtain the real needle region inside the body.

At block 312 of the method, the needle region inside and outside body may be combined (e.g., as referred to in block 104) to provide an accurate determination of the needle position (e.g., comprising trajectory or direction). An accuracy result may be selected to express the needle direction. For example, a comparison between the real needle direction and the planned needle direction may be used to determine the accuracy of the needle positioning.

As part of the procedure for determining the position of the needle, and hence the trajectory or direction of the needle, line fitting, at block 314, may be performed on the real needle region. The coordinate of a detected region i can be expressed as:

$$\{X,Y,Z\}\in\{(x_{i1},y_{i1},z_{i1}), \ldots (x_{ij},y_{ij},z_{ij})\},$$

which means that the number of points in candidate needle region i is j. By fitting the line using $\{X, Y, Z\}$, it is possible to obtain the point $(x_0, y_0, z_0)$ on the needle and the unit direction vector $(v_x, v_y, v_z)$ of the needle. This information can be used to construct a visual representation of the needle position for the image to be displayed on the user interface.

In some embodiments, the method 300 comprises, at block 316, detecting a tip of the needle based on a comparison of a measurement within a candidate needle tip region within the data with a threshold indicative of a lack of presence of needle structure within the candidate needle tip region.

In some embodiments, if the comparison with the threshold is indicative of needle structure being present in the candidate needle tip region, another candidate needle tip region is identified from the data to determine whether or not the other candidate needle tip region comprises data indicative of the presence of needle structure. If the comparison with the threshold is indicative of lack of presence of needle structure within the data corresponding to the candidate needle tip region, a previously-identified candidate needle tip region comprising data indicative of the presence of needle structure within the previously-identified candidate needle tip region is determined to contain the tip of the needle.

A further description of the needle tip detection procedure is given below.

In some embodiments, the method 300 comprises, at block 318, detecting an insertion point (e.g., 'entry point') on the body for the needle based on a first line fitted to a predicted trajectory of the needle determined based on the determined position of the needle and a second line fitted along a surface of the body.

A further description of the insertion point detection procedure is given below.

In some embodiments, the method 300 comprises, at block 320, causing a user interface to provide an indication of a difference between a predicted trajectory and a planned trajectory of the needle responsive to a determination that there is a deviation between the predicted trajectory and the planned trajectory. For example, the user may identify the deviation from the indication and, if appropriate, make a change to the interventional procedure to ensure that the target point is reached upon further insertion of the needle.

At block 322, the method 300 may end or at least partially repeat certain blocks of the method 300 (e.g., upon further data being received from the imaging apparatus).

Figure 4:
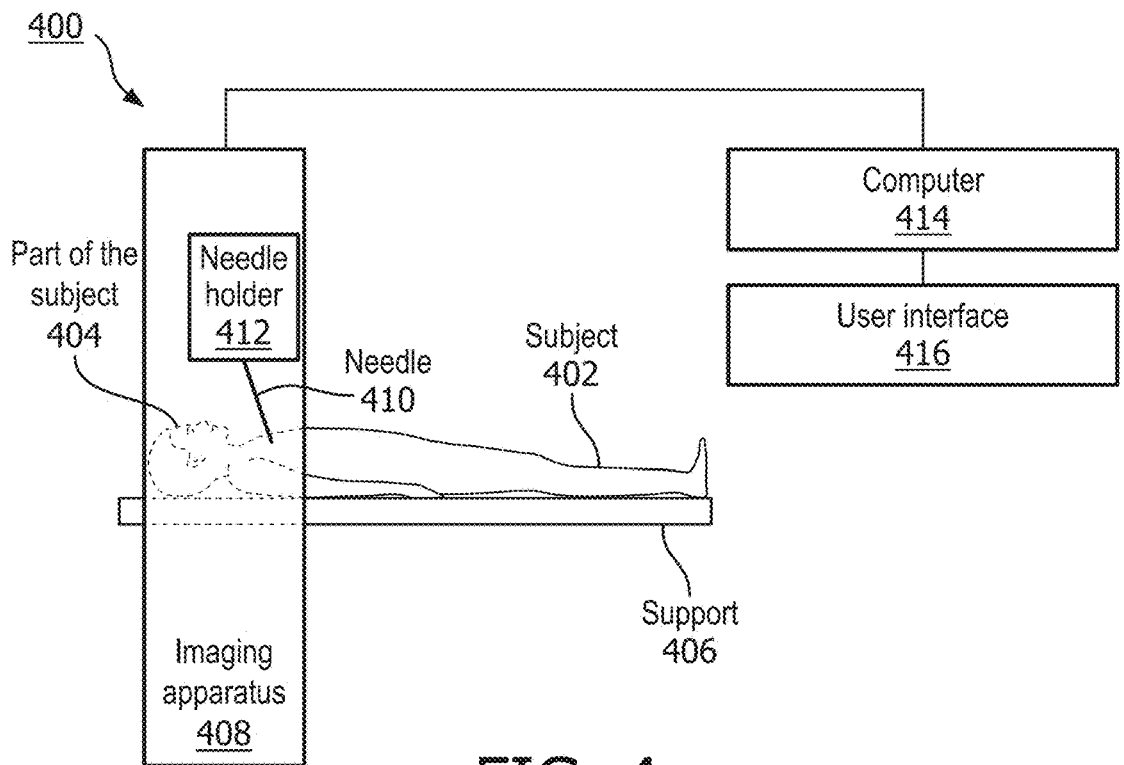
FIG. 4 is a schematic drawing of a system for determining a position of a needle according to an embodiment.

FIG. 4 depicts a system 400 for implementing certain methods described herein. The system 400 is used for obtaining the radiographic imaging slices are referred to in the method and performing certain blocks of the methods described herein.

In the system 400, an interventional procedure is depicted as being performed on a subject 402, in particular, on a certain part 404 of the subject's body (indicated by dashed lines in FIG. 4). The subject is supported by a support 406 such as a couch. The position of the support 406 may be controlled (e.g., by a computer) in relation to an imaging apparatus 408 (e.g., a CT imaging apparatus) of the system 400. The imaging apparatus 408 is used to obtain the radiographic imaging slices. For example, the imaging apparatus 408 may comprise an emitter (e.g., X-ray emitter, not shown) and a corresponding detector (not shown) that are mounted on a gantry (which may form part of the imaging apparatus 408), which can rotate to enable a series of measurements to be taken to obtain the data for constructing each radiographic imaging slice. The imaging apparatus 408 and the support 406 may be moved relative to each other to obtain multiple radiographic imaging slices.

An interventional procedure in which a needle 410 (e.g., supported by a needle holder 412) is inserted in the body of the subject 402 may be performed while obtaining the radiographic imaging slices.

The system 400 further comprises a computer 414 (e.g., a processing unit comprising processing circuitry) for implementing certain methods described herein. The computer 414 is communicatively coupled to a user interface 416 such as a display for visualizing the images obtained by the imaging apparatus 408 and/or displaying information generated or determined by the computer 414.

Although the system 400 may appear to depict the imaging apparatus 408, computer 414 and user interface 416 as being in the same location, in some cases, these components may be at the same or different locations. For example, the imaging apparatus 408 may be at a different location to the computer 414 and/or user interface 416. The computer 414 may be implemented by a user computer (e.g., connected to the same terminal as the user interface 416) or may be implemented by a server or cloud-based service.

Some experimental images as obtained according to certain methods or systems described herein are described below. For ease of reference, certain features corresponding to the features depicted in the system 400 are described by reference signs incremented by 100 for FIGS. 5a to 5b, 200 for FIGS. 6a to 6b, 300 for FIGS. 7a to 7b.

Figure 5A:
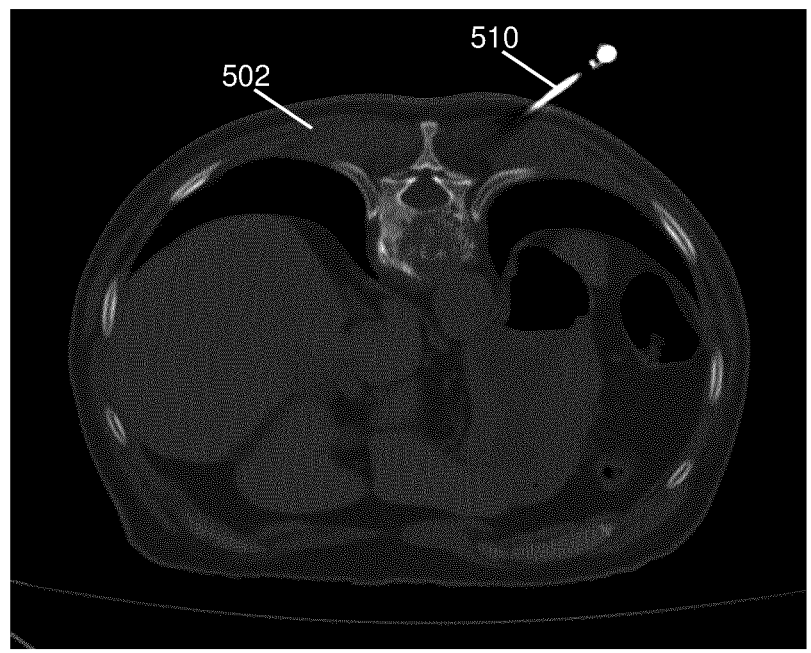
FIGS. 5a to 5b are images used in certain methods described in the embodiments.
Figure 5B:
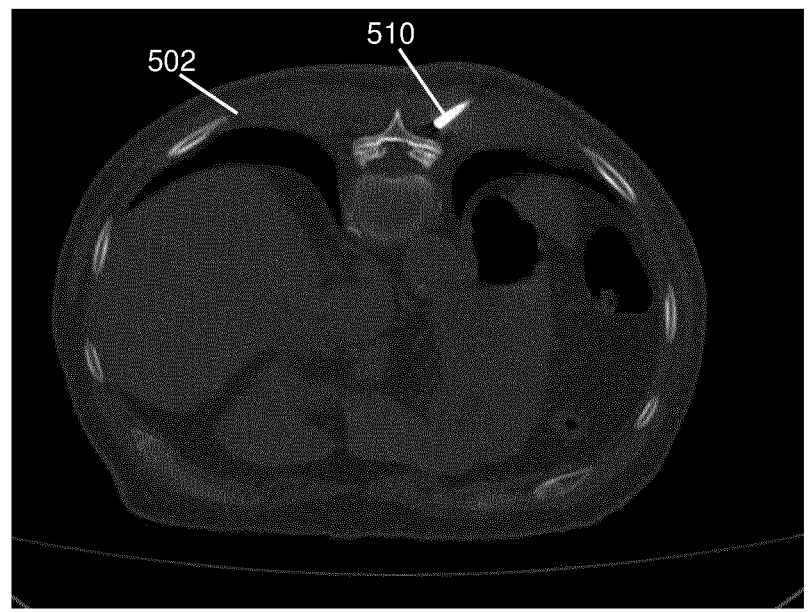

FIGS. 5a to 5b show different (CT) radiographic imaging slices obtained by an imaging apparatus (e.g., an imaging apparatus such as shown by FIG. 4) in the axial plane. FIGS. 5a to 5b show insertion of a needle 510 in the body of a subject 502. In FIG. 5a, a 'first' portion of needle 510 is visible outside the body. In FIG. 5b, a 'second' portion of needle 510 is visible inside the body. In this case, FIG. 5a refers to a seventh radiographic imaging slice and FIG. 5b refers to a tenth radiographic imaging slice from a plurality of radiographic imaging slices. Thus, a user may need to cycle between these different slices when attempting to manually determine the position of the needle 510.

Figure 6A:
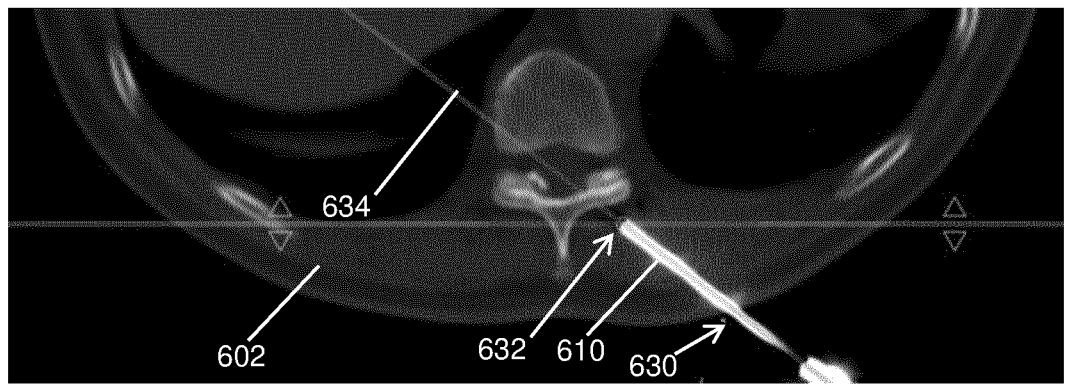
FIGS. 6a to 6b are images for visualizing a position of a needle according to an embodiment.
Figure 6B:
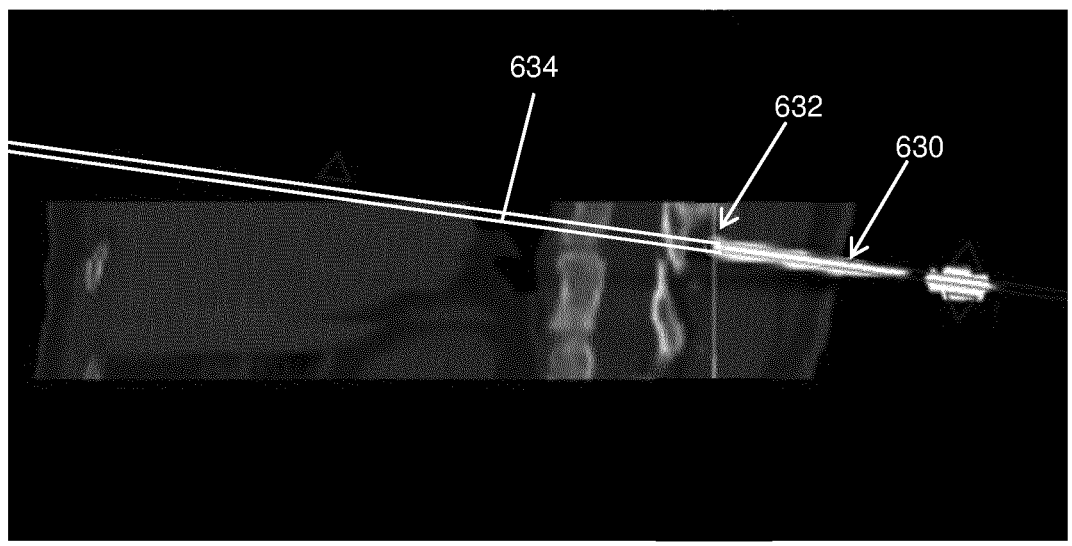

FIGS. 6a to 6b show further images where certain methods described herein have been implemented to enable visualization of the entire needle 610 within a single image. An entry point 630 on the surface of the body 602 and the needle tip position 632 can be identified in FIGS. 6a to 6b to assist the user in carrying out the interventional procedure. A line 634 indicating the trajectory of the needle 610 is also shown in FIGS. 6a to 6b.

Experimental data was obtained while implementing an interventional procedure on 31 patients (122 series) using certain methods described herein. The data was collected using different equipment (e.g., imaging apparatus) from different countries and includes different body parts, such as the chest, lumbar, abdomen, shoulder, etc. The accuracy rate of determining the needle position according to certain methods described herein was determined from this data. The accuracy rate of needle direction detection was found to be 100%, the accuracy of needle tip detection was found to be 91% and the accuracy of entry point detection was found to be 96%. Thus, certain methods described herein may provide accurate determination of needle position (e.g., including trajectory/direction, tip position and entry point of the needle), which may facilitate efficient and accurate implementation of an interventional procedure by a user.

Figure 7A:
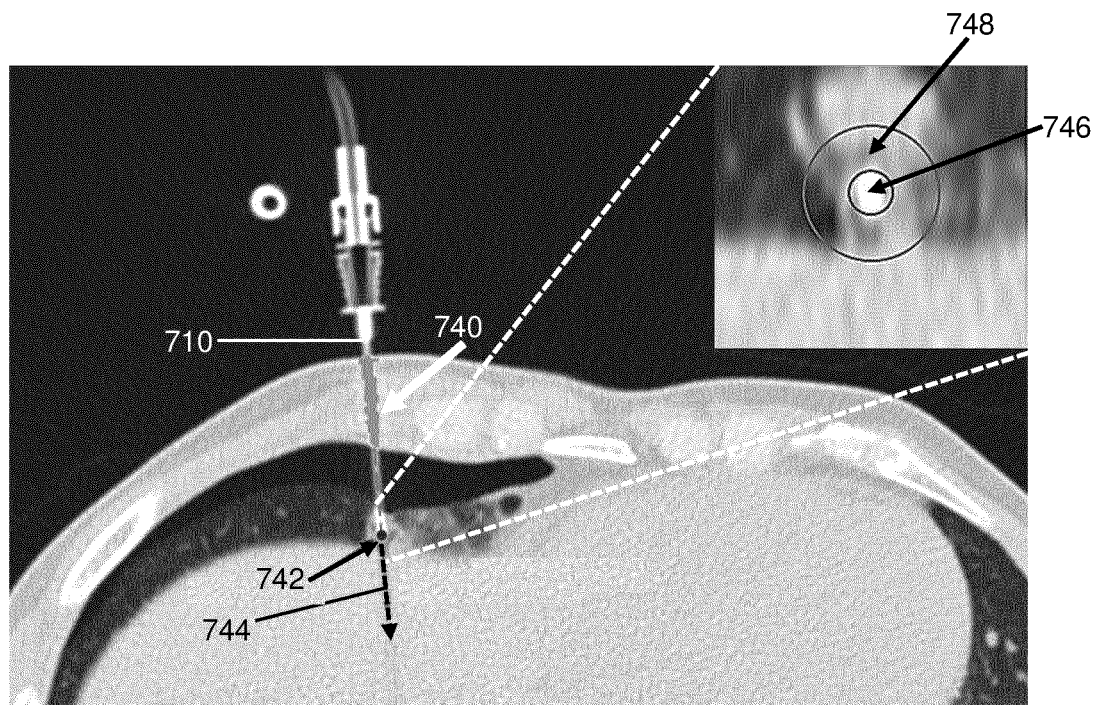
FIGS. 7a to 7b are images for visualizing a position of a needle according to an embodiment.
Figure 7B:
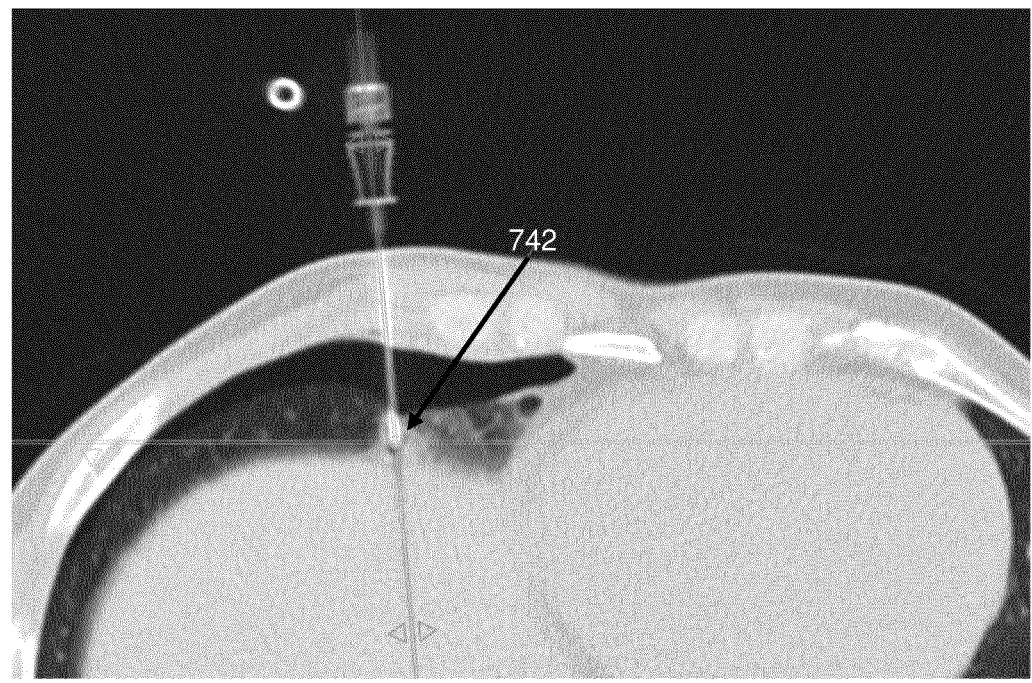

FIGS. 7a to 7b depict the implementation of the needle tip detection in relation to a radiographic imaging slice. The needle tip detection procedure may be based on segmentation 740 of the needle 710 (e.g., each slice may contain a segment of the needle 710). Thus, each candidate needle region may refer to a segment of the needle 710. Since the segmentation 740 may not necessarily identify the real needle tip position, an additional procedure may be used, as referred to in block 316, to identify the real needle tip 742.

In some embodiments, a (virtual) cylinder may be created to detect further needle structure if there is any in a candidate needle tip region. This cylinder is aligned along the best fitting straight line 744 of segmented needle part and comprises candidate needle tip regions. From the current end of needle segmentation forward, and within the cylinder, a determination is made whether there's still needle structure beyond segmentation. In other similar words, if a candidate needle tip region contains needle structure but an adjacent candidate needle tip region (forward from the previously analyzed needle tip region) does not contain needle structure then the previously analyzed needle tip region may be considered to contain the tip of the needle, thereby identifying the position of the tip 742 of the needle.

A further description of the needle tip identification is now given.

Where a candidate needle tip region is identified as containing needle structure, the method tracks along needle's direction (line 744). A difference in pixel value is calculated between a central region 746 (i.e., a candidate needle tip region) and its surrounding region 748 on each cross-section of the cylinder. If the difference is large enough (meaning the average CT pixel value of the central region 746 is much higher than the one of surrounding region), it is determined that there is still needle structure in the region. This difference is apparent from the embedded figure in FIG. 7a (showing in expanded form the part of the figure that contains the needle tip 742). The embedded figure in FIG. 7a shows in more detail the contrast between the central region 746 and the surrounding region 748. Thus, if there is still needle structure in the region, the tracking may continue. When no needle structure can be detected (due to a smaller or no differences between the central region 746 and the surrounding region 748), a determination is made the real needle tip 742 is reached (since no needle structure may be indicative of the needle tip having been reached in the previous region).

Figure 8A:
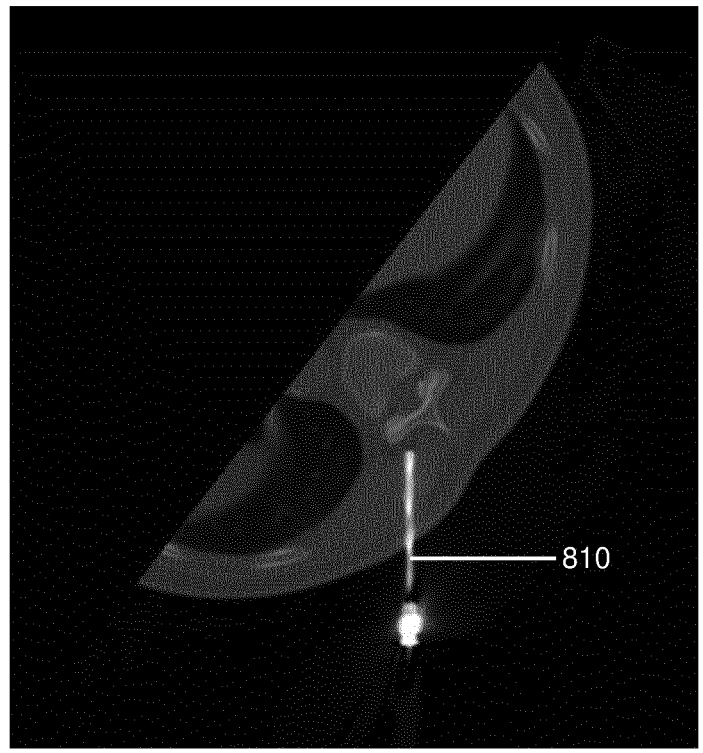
FIGS. 8a and 8b respectively show an image for visualizing a position of a needle and a corresponding illustration of determining a position of the needle according to an embodiment.
Figure 8B:
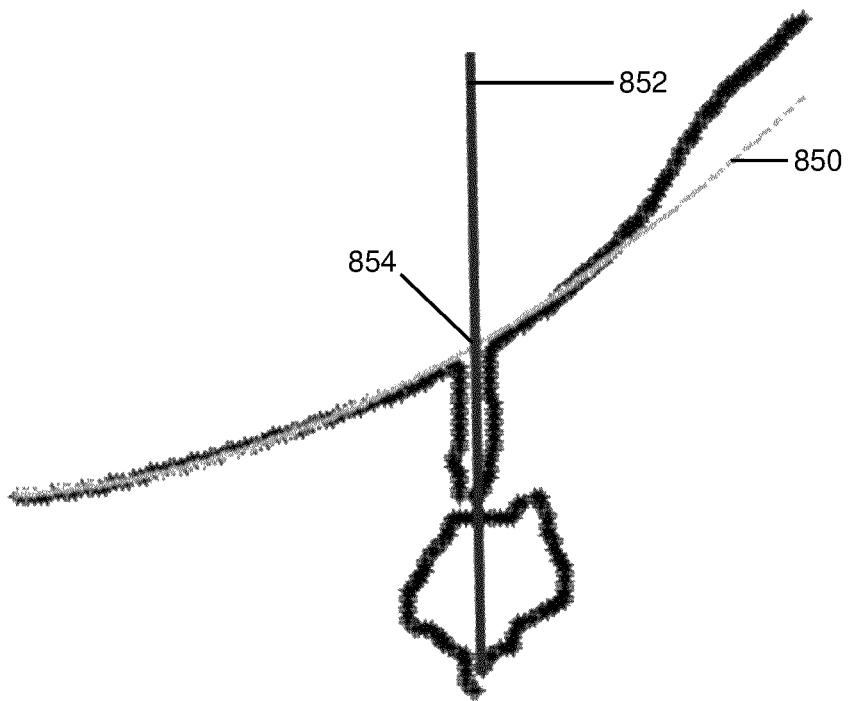

FIGS. 8a to 8b depict the implementation of the needle entry point detection in relation to a radiographic imaging slice. In this embodiment, the needle entry point detection involves fitting two lines to certain structures identified in the radiographic imaging slice and identifying an intersection point of the two lines. The implementation of the needle entry point detection of this embodiment is described below.

Volume data is reconstructed perpendicular to the direction of needle 810. The sagittal plane (as in FIG. 8a but other planes such as the axial plane or coronal plane may be used) of the reconstructed volume data includes the whole needle based on the three-dimensional coordinates of the needle 810. Thus, a line (e.g., a linear line) can be fitted to the reconstructed volume data.

The surface of the body can be detected based on the needle direction in the image. A line 850 (e.g., curve as shown in FIG. 8b) is fitted along the surface of the subject's body according to the quadratic curve equation:

$$y=ax^2+bx+c$$

where it assumed that the surface of the body in the sagittal plane can be represented by such an expression. In other cases, a different expression such as a linear line equation may be used depending on the shape of the surface of the body.

As referred to above, the needle in the sagittal plane can be regarded as a linear (two-dimensional) line 852 and the equation of straight line is known based on the needle region, according to the linear line equation:

$$y=kx+d$$

By combining the above expressions, it may be possible to determine the intersection point which corresponds to the needle entry point 854. In some cases, the entry point may need to be fine-tuned by further image processing analysis as the surface of the body may not be smooth and/or may not correspond to a quadratic equation.

The above methods and system refer to a method of determining a needle position. Another method of determining a needle position is described below and may be implemented by the system 400 of FIG. 4.

Figure 9:
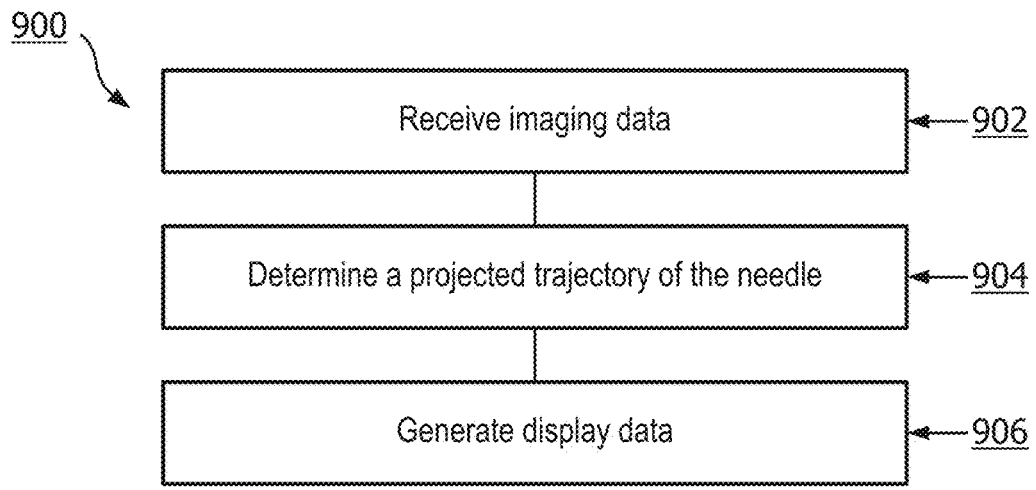
FIG. 9 refers to a method of determining a position of a needle according to an embodiment.

FIG. 9 shows a method 900 (e.g., a computer-implemented method) of determining a needle position in a body of a subject and/or facilitating visualization of the position of the needle. The method 900 may be implemented by a computer such as a user computer communicatively coupled to a user interface, or a server or cloud-based service (e.g., communicatively coupled to the user computer and/or user interface). The method 900 may be implemented as part of or conjunction with any other methods described herein.

The method 900 comprises, at block 902, receiving data corresponding to at least one radiographic imaging slice of a body comprising information indicative of a position of a needle inserted in the body. The data received at block 902 may correspond to the data received at block 102 of the method 100.

The method 900 comprises, at block 904, determining a predicted trajectory of the needle based on the information. The predicted trajectory may be determined using certain methods described herein such as using the method 100.

The method 900 comprises, at block 906, generating display data for providing a visual representation of the needle in an image plane parallel to a line comprising the predicted trajectory of the needle. The image plane may be tilted with respect to the at least one radiographic imaging slice of the body. Thus, the user may select an image view (e.g., based on an MPR image or a three-dimensional reconstruction of the body) at any angle and the needle may be shown in full in the image. Since certain methods described herein (e.g., method 100) may enable the position of the needle to be determined (and hence its direction, tip location and entry point), it may be possible to include a visual representation of the needle within any image place selected by the user. In cases where the needle is at an angle to the plane of the radiographic imaging slice (e.g., in the axial plane), it may be possible to digitally tilt the image in order to visualize the entire needle in the body. For example, the image (corresponding to the display data) is in a plane that is digitally tilted with respect to a plane parallel to the at least one radiographic imaging slice. In other words, the generated display data for the image is such that it may be possible to visualize at least part of the needle in a digitally-reconstructed plane at an angle to the plane of the radiographic imaging slice. The tilt/angle may be varied according to a user need. This may avoid the need to perform a physical tilt where the gantry of the imaging apparatus is tilted and aligned with the needle to image the entire needle, which may save time.

The digital tilt procedure may be used instead of the physical tilt procedure. Digital tilt may facilitate needle visualization in a specified or preferred direction/plane, which may provide a flexible, intuitive and/or convenient needle visualization. Further, an accurate (or exact) angle and depth of the needle may be determined using the digital tilt procedure and may fully represent the actual needle path during an interventional procedure. The path may be adjusted at any time, and the scanning range may be precisely positioned to control the scanning dose delivered by the imaging apparatus, so that accurate sampling can be taken to create a basis for the pathological diagnosis of a lesion, and also to reduce unnecessary radiation damage for the subject.

The digital tilt procedure may involve planning an interventional procedure (i.e., positioning of a lesions and design of the puncture path) and confirmation. By automatically identifying the actual puncture path and presenting the path image, the current needle position, direction, and needle angle may be confirmed. Such information may be useful for determining the needle tip distance from the lesion location.

Figure 10:
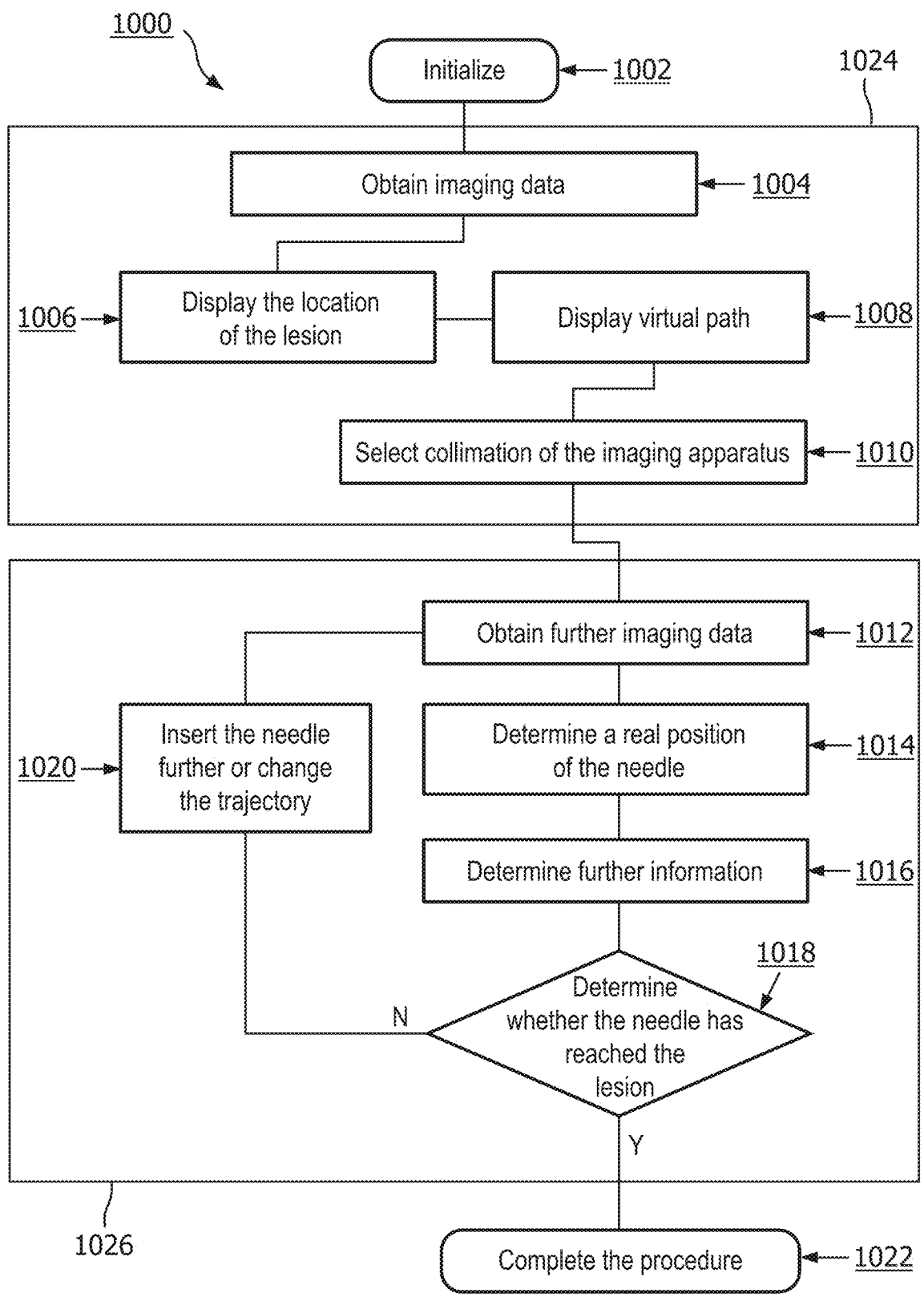
FIG. 10 refers to a method of determining a position of a needle according to an embodiment.

FIG. 10 shows a method 1000 (e.g., a computer-implemented method) of determining a needle position in a body of a subject. The method 1000 may be implemented by a computer such as a user computer communicatively coupled to a user interface, or a server or cloud-based service (e.g., communicatively coupled to the user computer and/or user interface). In some embodiments, the method 1000 comprises the method 900. Reference may be made to any of the other methods described herein, which may be used to facilitate or implement the method 1000. In some embodiments, not all of the blocks are implemented by a computer (e.g., they may be implemented by a user). Thus, the computer-implemented part of the method 1000 may refer to any blocks which can be implemented by the computer rather than the user.

The method 1000 is initialized at block 1002. Further blocks of the method 1000 are described below.

At block 1004 of the method 1000, data corresponding to radiographic imaging slices is obtained (e.g., by causing the imaging apparatus to obtain the slices). These slices may be received and loaded by a computer (e.g., computer 414) for display on a user interface (e.g., user interface 416).

The design of a virtual interventional path is now described.

In some embodiments, a scan is performed using the imaging apparatus. The obtained data may be reconstructed to obtain a (e.g., thin slice) MPR image, which may be load into an application (e.g., for visualization on the user interface). The application may be used to display axial, sagittal, and coronal MPR images.

At block 1006 of the method 1000, the displayed image is used to view the location of the lesion. The user may select the entry needle point and determine the virtual interventional path design.

At block 1008 of the method 1000, the virtual path may be displayed and saved by the application. Any MPR images (such as the sagittal tilt) may also include the virtual path for the needle.

At block 1010 of the method 1000, the collimation of the imaging apparatus may be selected according to a specified radiation dose and may be based on the virtual needle path. If less radiation can be delivered by using the collimation function, the dose delivered to the subject may be reduced. In some cases, the width of the radiation delivered by the imaging apparatus may be in the range 2 to 4 cm.

Selecting the appropriate collimation range according to the virtual path and the lesion position may improve the efficiency of the procedure. During the actual puncture process (described below), the needle may be continuously probed and the same lesion position may be scanned multiple times.

As part of a verification procedure, further radiographic imaging slices may be obtained at block 1012 of the method 1000 (e.g., corresponding to block 1004 but may depend on the collimation determined at block 1010). As part of this procedure, the real needle position may be determined as described below.

At block 1014 of the method 1000, the real position of the needle is determined in accordance with certain methods described herein. The real needle path and the virtual path may be displayed on the user interface.

At block 1016 of the method 1000, further information can be determined from the real position of the needle. For example, the distance between the needle tip and the lesion location and/or a deviation between the real needle trajectory and the trajectory of the virtual path.

The verification procedure may continue/repeat, as determined at block 1018 of the method 1000) if it is determined that the needle has not yet reached the lesion. If appropriate, the user may cause, at block 1020, the needle to be inserted further and/or the trajectory of the needle changed in order to reach the lesion location.

The procedure may be considered to be completed, at block 1022, once the needle has reached the lesion.

In some embodiments, there may be two parts to the method 1000. In FIG. 10, a first part 1024 (comprising blocks 1004 to 1010) of the procedure comprises 'planning' the interventional procedure and a second part 1026 (comprising blocks 1012 to 1020) of the procedure comprises 'verifying' the interventional procedure.

While implementing certain blocks of the method 1000, the interventional procedure may involve any of the following procedures.

In some implementations, the position of the couch (see FIG. 4) may be determined relative to the position of the needle, which may simplify implementation of the interventional procedure. According to the virtual puncture path, the method 1000 may comprise automatically calculating the position of the couch at the needle tip position and the lesion position. Based on the saved position of the couch, it may be possible to determine which part of the subject's body is being imaged while also maintaining control over the position of the needle relative to the lesion position. Thus, in some embodiments, the couch may be directly controlled so as to be directed to a specified position according to the calculated result of the virtual path. A laser or other pointer may be used to indicate the entry point on the body (e.g., according to the laser positioning line). The user may then cause the needle to approach the entry point and be inserted into the body.

In some implementations, the real needle trajectory may be automatically recognized and displayed on the user interface. For example, after the needle is inserted, the collimation function may be used for multiple scans to reduce the dose and the imaging slices may be automatically loaded into the application to enable the needle trajectory to be determined. In some operations, it may not be possible to adjust the gantry and/or couch angle by physical tilt. Thus, the digital tilt method described above may be used. Thus, the user may not need to adjust the gantry angle and/or the couch angle. The method 1000 may automatically recognize the needle trajectory and display the needle trajectory image, which may simplify the procedure for the user.

In some implementations, it may be possible to automatically measure related parameters to simplify the workflow for the user. For example, when the needle is inserted, the needle angle may not be precisely controlled, resulting in a cross-layer phenomenon on the image. This may cause issues in confirming the needle position. The method 1000 may provide automatic identification of the needle position, the distance from the needle tip to the lesion position, the actual path and the virtual design. Certain information such as needle path angle deviation (e.g., in combination with the predicted needle trajectory) may be displayed on the user interface. This information may be used by the user to visually confirm the position of the needle in the tissue, for example, so as to facilitate active path adjustment at any time during the procedure. Thus, it may be possible to accurately position the needle at the lesion, which may facilitate accurate pathological diagnosis.

Figure 11:
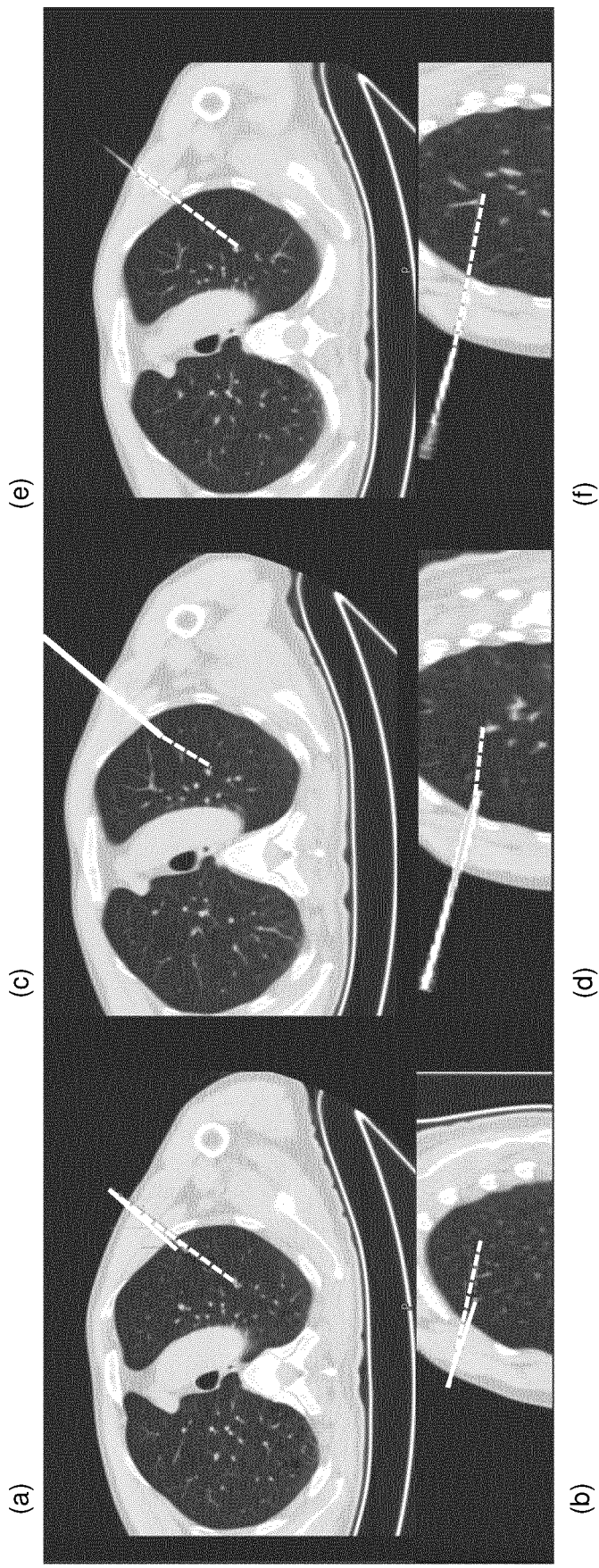
FIG. 11 shows images for visualizing a position of a needle according to an embodiment.

FIG. 11 shows a series of images such as may be displayed on the user interface described herein when implementing the method 1000. The upper row shows images in the axial plane while the lower row shows corresponding images in the sagittal plane. The images in left hand column (labelled (a) and (b)) show the virtual (planned) and real (tracked) needle paths in the axial and sagittal planes, respectively. The images in the center column (labelled (c) and (d)) show the real (tracked) needle path. The images in the right hand column (labelled (e) and (f)) show the virtual (planned) needle path. In FIG. 11, guidelines for the user in the images are represented by white 'guide' lines. The dashed white lines refer to the virtual, or planned, needle path. The solid white lines refer to the real, or tracked, needle path. When displaying the images, the 'guide' lines may be colored. For example, the planned needle path may be shown as 'blue' and the tracked needle path may be 'green'. Any combination of colors may be used. Further, the lines may be of a different thickness and/or dotted or dashed to provide guidance for the user. When planning and performing an interventional procedure, the user may find the various lines (or other markers) useful for guiding them during the procedure.

Figure 12:
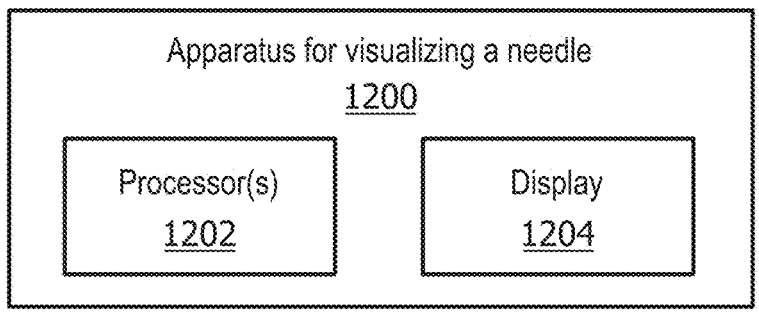
FIG. 12 is a schematic drawing of an apparatus for determining a position of a needle according to an embodiment.

FIG. 12 shows an apparatus 1200 for visualizing a needle inserted in a body. The apparatus 1200 comprises a processing unit 1202 (which may correspond to the computer 414 of FIG. 4) configured to implement certain methods described herein (e.g., to determine a position of the needle). The apparatus 1200 further comprises a display unit 1204 (which may correspond to the user interface 416 of FIG. 4) configured to display an image of the body superimposed with the position of the needle.

Figure 13:
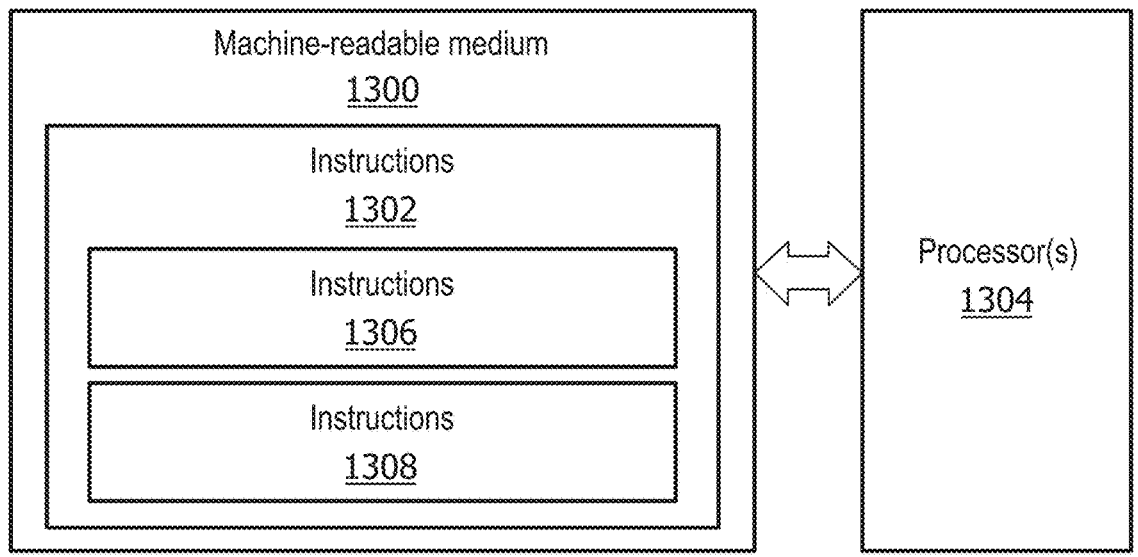
FIG. 13 is a schematic drawing of a machine-readable medium for determining a position of a needle according to an embodiment.

FIG. 13 shows a tangible machine-readable medium 1300. The tangible machine-readable medium 1300 comprises instructions 1302 which, when executed on at least one processor 1304, cause the at least one processor 1304 to implement certain methods described herein. In this embodiment, the instructions 1302 comprise instructions 1306 which are configured to implement block 102 of the method 100. The instructions 1302 further comprise instructions 1308 which are configured to implement block 104 of the method 100. Any of the methods described herein may be implemented by virtue of tangible machine-readable medium 1300 causing the at least one processor 1304 to implement such methods.

In some cases, any of the modules, processing circuitry or processing units described above (e.g., computer 414 and/or processing unit 1202) may comprise at least one dedicated processor (e.g., an application specific integrated circuit (ASIC) and/or field programmable gate array (FPGA), etc.) for implementing the functionality of the module.

While the invention has been illustrated and described in detail in the drawings and foregoing description, such illustration and description are to be considered illustrative or exemplary and not restrictive; the invention is not limited to the disclosed embodiments.

One or more features described in one embodiment may be combined with or replace features described in another embodiment. For example, the methods 100, 200, 300, 900 and 1000 may be modified based on features described in relation to the system 400, apparatus 1200 and/or the machine-readable medium 1300, and vice versa.

Embodiments in the present disclosure can be provided as methods, systems or as a combination of machine-readable instructions and processing circuitry. Such machine-readable instructions may be included on a non-transitory machine (for example, computer) readable storage medium (including but not limited to disc storage, CD-ROM, optical storage, etc.) having computer readable program codes therein or thereon.

The present disclosure is described with reference to flow charts and block diagrams of the method, devices and systems according to embodiments of the present disclosure.

Although the flow charts described above show a specific order of execution, the order of execution may differ from that which is depicted. Blocks described in relation to one flow chart may be combined with those of another flow chart. It shall be understood that each block in the flow charts and/or block diagrams, as well as combinations of the blocks in the flow charts and/or block diagrams can be realized by machine readable instructions.

The machine readable instructions may, for example, be executed by a general purpose computer, a special purpose computer, an embedded processor or processors of other programmable data processing devices to realize the functions described in the description and diagrams. In particular, a processor or processing circuitry, or a module thereof, may execute the machine readable instructions. Thus functional modules of apparatus (for example, the processing unit 1202) and other devices described herein may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine readable instructions may also be stored in a computer readable storage that can guide the computer or other programmable data processing devices to operate in a specific mode.

Such machine readable instructions may also be loaded onto a computer or other programmable data processing devices, so that the computer or other programmable data processing devices perform a series of operations to produce computer-implemented processing, thus the instructions executed on the computer or other programmable devices realize functions specified by block(s) in the flow charts and/or in the block diagrams.

Further, the teachings herein may be implemented in the form of a computer program product, the computer program product being stored in a storage medium and comprising a plurality of instructions for making a computer device implement the methods recited in the embodiments of the present disclosure.

Elements or steps described in relation to one embodiment may be combined with or replaced by elements or steps described in relation to another embodiment. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for visualizing a needle inserted in a body, comprising:
   receiving data corresponding to a plurality of radiographic imaging slices of the body;
   determining a position of the needle inserted in the body based on combining information from at least one of the radiographic imaging slices comprising an indication of a first portion of the needle outside the body and at least one other of the radiographic imaging slices comprising an indication of a second portion of the needle inside the body, wherein determining the position of the needle comprises generating a combined needle region by merging data corresponding to a position of the first portion of the needle outside the body with data corresponding to a position of the second portion of the needle inside the body; and
   generating display data for providing a visual representation of the needle in an image of the body in combination with a visual representation of at least the first and second portions of the needle superimposed on the image, wherein the image is in a plane that is digitally tilted with respect to a plane parallel to the plurality of radiographic imaging slices.

2. The method of claim 1, further comprising causing a user interface to display the image.

3. The method of claim 2, further comprising:
   identifying the second portion of the needle inside the body by performing threshold truncation on the received data corresponding to the second portion of the needle; and
   determining a three-dimensional region corresponding to the second portion of the needle based on a planned path for the needle, wherein the three-dimensional region comprises a plurality of candidate needle regions from which the real needle region can be determined.

4. The method of claim 3, comprising extending the three-dimensional region corresponding to the second portion of the needle by searching for at least one neighboring candidate needle region removed by the threshold truncation and including data corresponding to a neighboring candidate needle region as part of the extended three-dimensional region.

5. The method of claim 1, wherein determining the position of the needle comprises fitting a line to a plurality of regions in the received data indicative of the position of the first and second portions of the needle.

6. The method of claim 1, wherein determining the position of the needle comprises determining a real needle region from a plurality of candidate needle regions by minimizing an energy function derived from the received data.

7. The method of claim 6, wherein the energy function is based on at least one of: a discrete degree of the candidate needle region; an area of the candidate needle region; an average pixel value of an edge of the candidate needle region; an average pixel value of an inner part of the candidate needle region; a mean of all cross-sectional values of the candidate needle region; a circularity parameter; and a deviation parameter.

8. The method of claim 1, further comprising:
   identifying the first portion of the needle outside the body by performing morphological opening on the received data corresponding to the first portion of the needle; and determining a three-dimensional region corresponding to the first portion of the needle based on a planned path for the needle, wherein the three-dimensional region comprises a plurality of candidate needle regions from which the real needle region can be determined.

9. The method of claim 1, comprising detecting a tip of the needle based on a comparison of a measurement within a candidate needle tip region within the data with a threshold indicative of a lack of presence of needle structure within the candidate needle tip region.

10. The method of claim 9, wherein:
if the comparison with the threshold is indicative of needle structure being present in the candidate needle tip region, another candidate needle tip region is identified from the data to determine whether or not the other candidate needle tip region comprises data indicative of the presence of needle structure; and
if the comparison with the threshold is indicative of lack of presence of needle structure within the data corresponding to the candidate needle tip region, a previously-identified candidate needle tip region comprising data indicative of the presence of needle structure within the previously-identified candidate needle tip region is determined to contain the tip of the needle.

11. The method of claim 1, comprising detecting an insertion point on the body for the needle based on a first line fitted to a predicted trajectory of the needle determined based on the determined position of the needle and a second line fitted along a surface of the body.

12. The method of claim 1, comprising causing a user interface to provide an indication of a difference between a predicted trajectory and a planned trajectory of the needle responsive to a determination that there is a deviation between the predicted trajectory and the planned trajectory.

13. An apparatus for visualizing a needle inserted in a body, the apparatus comprising:
a memory that stores a plurality of instructions;
a processor that couples to the memory and is configured to execute the plurality of instructions to:
receive data corresponding to a plurality of radiographic imaging slices of the body;
determine a position of the needle inserted in the body based on combining information from at least one of the radiographic imaging slices comprising an indication of a first portion of the needle outside the body and at least one other of the radiographic imaging slices comprising an indication of a second portion of the needle inside the body, wherein determining the position of the needle comprises generating a combined needle region by merging data corresponding to a position of the first portion of the needle outside the body with data corresponding to a position of the second portion of the needle inside the body; and
generate display data for providing a visual representation of the needle in an image of the body in combination with a visual representation of at least the first and second portions of the needle superimposed on the image, wherein the image is in a plane that is digitally tilted with respect to a plane parallel to the plurality of radiographic imaging slices; and
a display configured to display the image of the body superimposed with the position of the needle.

14. A non-transitory computer-readable medium for storing executable instructions, which cause a computer-implemented method to be performed to visualize a needle inserted in a body, the method comprising:
receiving data corresponding to a plurality of radiographic imaging slices of the body;
determining a position of the needle inserted in the body based on combining information from at least one of the radiographic imaging slices comprising an indication of a first portion of the needle outside the body and at least one other of the radiographic imaging slices comprising an indication of a second portion of the needle inside the body, wherein determining the position of the needle comprises generating a combined needle region by merging data corresponding to a position of the first portion of the needle outside the body with data corresponding to a position of the second portion of the needle inside the body; and
generating display data for providing a visual representation of the needle in an image of the body in combination with a visual representation of at least the first and second portions of the needle superimposed on the image, wherein the image is in a plane that is digitally tilted with respect to a plane parallel to the plurality of radiographic imaging slices.

* * * * *